(12) United States Patent
Knapton et al.

(10) Patent No.: US 9,382,275 B2
(45) Date of Patent: Jul. 5, 2016

(54) PREPARATION OF PHOSPHORUS—CONTAINING ANTIWEAR COMPOSITION FOR USE IN LUBRICANT COMPOSITIONS

(75) Inventors: Daniel J. Knapton, Willowick, OH (US); William R. S. Barton, Belper (GB); David J. Aaserud, Painesville, OH (US)

(73) Assignee: The Lubrizol Corporation, Wickliffe, OH (US)

( * ) Notice: Subject to any disclaimer, the term of this patent is extended or adjusted under 35 U.S.C. 154(b) by 607 days.

(21) Appl. No.: 13/819,361

(22) PCT Filed: Aug. 24, 2011

(86) PCT No.: PCT/US2011/048917
§ 371 (c)(1),
(2), (4) Date: Apr. 29, 2013

(87) PCT Pub. No.: WO2012/030594
PCT Pub. Date: Mar. 8, 2012

(65) Prior Publication Data
US 2015/0307527 A1    Oct. 29, 2015

Related U.S. Application Data

(60) Provisional application No. 61/378,425, filed on Aug. 31, 2010.

(51) Int. Cl.
*C10M 137/08* (2006.01)
*C07F 9/09* (2006.01)
*C10M 137/04* (2006.01)

(52) U.S. Cl.
CPC . *C07F 9/09* (2013.01); *C07F 9/093* (2013.01); *C10M 137/04* (2013.01); *C10M 137/08* (2013.01); *C10M 2205/026* (2013.01); *C10M 2205/0285* (2013.01); *C10M 2207/282* (2013.01); *C10M 2209/084* (2013.01); *C10M 2215/04* (2013.01); *C10M 2215/086* (2013.01); *C10M 2223/04* (2013.01); *C10M 2223/043* (2013.01); *C10N 2230/06* (2013.01); *C10N 2230/12* (2013.01); *C10N 2260/14* (2013.01)

(58) Field of Classification Search
CPC ............. C10M 137/08; C10M 137/04; C10M 2205/026; C10M 2205/0285; C10M 2215/04; C10M 2215/086; C10M 2223/04; C10M 2223/043; C07F 9/09; C07F 9/093; C10N 2230/06; C10N 2230/12; C10N 2230/14

USPC ................................... 508/424; 558/113, 177
See application file for complete search history.

(56) References Cited

U.S. PATENT DOCUMENTS

| | | | |
|---|---|---|---|
| 2,411,671 A | 11/1946 | Smith et al. | |
| 2,452,693 A * | 11/1948 | Smith et al. | ........ C10M 171/004 508/423 |
| 3,197,405 A | 7/1965 | LeSuer | |
| 3,215,715 A * | 11/1965 | Wurstner | .................. C07F 9/09 252/389.2 |
| 4,294,728 A * | 10/1981 | Vanlerberghe | ......... A61K 8/345 424/70.19 |
| 4,888,437 A * | 12/1989 | Zeidler | .................... A61K 8/06 558/105 |
| 4,957,649 A | 9/1990 | Ripple et al. | |
| 6,010,986 A | 1/2000 | Stachew et al. | |
| 6,468,946 B2 * | 10/2002 | Vinci | .................. C10M 137/00 508/398 |
| 2010/0016188 A1 | 1/2010 | Ramsey et al. | |

FOREIGN PATENT DOCUMENTS

| | | |
|---|---|---|
| JP | 03-247697 A | 11/1991 |
| JP | 06-247990 A | 9/1994 |
| JP | 07-138270 A | 5/1995 |
| WO | 02/102945 | 12/2002 |
| WO | 03/076557 | 9/2003 |
| WO | 2008/093759 | 8/2008 |
| WO | WO 2010011702 A1 * | 1/2010 ........... C10M 137/06 |

OTHER PUBLICATIONS

Written Opinion from corresponding International Application No. PCT/US2011/048917 dated Jan. 23, 2012.
Corresponding International Publication No. WO 2012/030594 A1 and Search Report published Mar. 8, 2012.

* cited by examiner

*Primary Examiner* — James Goloboy
(74) *Attorney, Agent, or Firm* — David M. Shold; Teresan W. Gilbert

(57) ABSTRACT

A process is provided for preparing a salt of a hydroxy-substituted di-ester of phosphoric acid, comprising: (a) reacting a phosphating agent with a monohydric alcohol and with an alkylene polyol, wherein the mole ratio of monohydric alcohol:alkylene polyol is about 0.2:0.8 to about 0.8:0.2 and wherein an excess of the phosphating agent is employed such that the product mixture formed thereby contains phosphorus acid functionality; and (b) reacting the product mixture of step (a) with an amine. The product is useful as an antiwear agent.

20 Claims, No Drawings

PREPARATION OF PHOSPHORUS—CONTAINING ANTIWEAR COMPOSITION FOR USE IN LUBRICANT COMPOSITIONS

BACKGROUND OF THE INVENTION

The disclosed technology relates to an antiwear agent and lubricating compositions thereof, and an improved method for preparing the antiwear agent. The invention further provides for a method of lubricating a driveline device or a grease application by employing a lubricating composition containing the antiwear agent. The lubricating compositions are also useful in industrial lubrication and metalworking applications.

Driveline power transmitting devices (such as gears or transmissions, especially axle fluids and manual transmission fluids (MTFs)) and grease applications, present highly challenging technological problems and solutions for satisfying the multiple and often conflicting lubricating requirements, while providing durability and cleanliness.

The development of new antiwear chemistry for such applications as gear oils has been driven by the desire to provide chemistries that meet modern lubricating requirements, provide thermo-oxidative stability and cleanliness, and have non-objectionable odor. Many current phosphorus antiwear or extreme pressure additives contain sulfur. Due to increasing environmental concerns, the presence of sulfur in antiwear or extreme pressure additives is becoming less desirable. In addition, many of the sulfur-containing antiwear or extreme pressure additives evolve volatile sulfur species, resulting in lubricating compositions containing antiwear or extreme pressure additives having an odor, which may also be detrimental to the environment or evolve emissions that may be higher than increasingly tighter health and safety legislation specifies.

One development in recent years to address some of these problems is disclosed in PCT Publication WO 2008/094759, Aug. 7, 2008, Ramsey, which reports a lubricating composition of an oil of lubricating viscosity and a sulfur-free amine salt of either (i) a hydroxyl-substituted diester of phosphoric acid, or (ii) a phosphorylated hydroxy-substituted di- or tri-ester of phosphoric acid. In one embodiment, the salt of a hydroxy-substituted diester of phosphoric acid may be prepared by a process comprising (i) reacting a phosphorylating agent with an alcohol, to form a mono- and/or diphosphate ester; reacting the phosphate ester with an alkylene oxide, to form a hydroxy-substituted diester of phosphoric acid; and salting the hydroxy-substituted diester of phosphoric acid with an amine and/or metal.

U.S. Pat. No. 2,411,671, Smith et al., Nov. 26, 1946, discloses a mineral oil composition resistant to foaming and a method of suppressing foaming, by incorporating an alkyl alkylene diphosphate having the following formula:

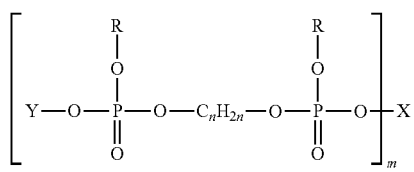

wherein R represents an alkyl group containing 1 to 18 carbon atoms, Y is a substituent of the class consisting of monovalent metals and alkyl groups, X represents a constituent of the class consisting of metals and an organic ammonium group derived from the class consisting of heterocyclic nitrogen bases and dialkylaryl amines, m is a number corresponding to the valence of X, and n is 2 to 6. An example is said to describe the preparation of dimethylaniline tri-octyl ethylene di-phosphate anti-foam agent. The amount of the salt may be between 0.01 and 1.0 percent by weight of the composition.

There is a continuing desire to improve the process for preparing material such as those described in WO 2008/094759. In particular, a process is desired which avoids the need to handle propylene oxide, minimizes the undesirable oligomerization of propylene oxide, and leads to higher conversion to desirable products with shorter reaction time.

The disclosed technology, therefore, solves one or more of the above-identified problems by use of the process as described hereinafter.

SUMMARY OF THE INVENTION

The disclosed technology provides a process for preparing a salt of a hydroxy-substituted di-ester of phosphoric acid, comprising: (a) reacting a phosphating agent with a monohydric alcohol and with an alkylene polyol, wherein the mole ratio of monohydric alcohol:alkylene polyol is about 0.2:0.8 to about 0.8:0.2, whereby the product mixture formed thereby contains phosphorus acid functionality (that is, not all the P—OH groups are esterified); and (b) reacting the product mixture of step (a) with an amine. In one embodiment the amine comprises at least one alkyl primary amine or at least one alkyl secondary amine. In one embodiment, an excess of the phosphating agent may be employed.

The disclosed technology also provides the use of the above process to prepare an antiwear agent.

The disclosed technology also provides the product prepared by the above-mentioned process, and a lubricant comprising an oil of lubricating viscosity and the product so prepared. The technology also provides a method for lubricating a gear, an axle, or a transmission, comprising supplying thereto such a lubricant.

The disclosed technology also provides a composition comprising an alkyl primary amine salt or an alkyl secondary amine salt of a phosphorus-containing composition which comprises at least some molecules represented by the formulas

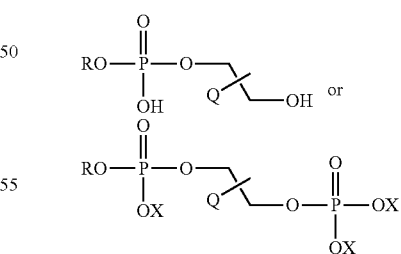

where R is an alkyl group having 4 to 20 carbon atoms, each Q is independently an alkyl group, and each X is independently R, or H, or a —R'OH group where R' is an alkylene group of 2 to 6 carbon atoms, provided that at least one X is H, further provided that said composition is substantially free from species containing a dimeric or oligomeric moiety derived from the dimerization of oligomerization of an alkylene oxide.

The disclosed technology also provides the use of the product as described herein to impart antiwear performance to a lubricant composition.

DETAILED DESCRIPTION OF THE INVENTION

Various preferred features and embodiments will be described below by way of non-limiting illustration.

The disclosed technology provides a process for preparing a salt of a hydroxy-substituted di-ester of phosphoric acid, comprising: (a) reacting a phosphating agent with a monohydric alcohol and with an alkylene polyol, wherein the mole ratio of monohydric alcohol:alkylene polyol is about 0.2:0.8 to about 0.8:0.2 and wherein an excess of the phosphating agent is employed such that the product mixture formed thereby contains phosphorus acid functionality; and (b) reacting the product mixture of step (a) with an amine.

The phosphating agent which may be employed is typically phosphorus pentoxide or a reactive equivalent thereof. Phosphorus pentoxide is usually referred to as $P_2O_5$, which is its empirical formula, even though it is believed to consist at least in part of more complex molecules such as $P_4O_{10}$. Both such materials have phosphorus in its +5 oxidation state. Other phosphorus materials that may be employed include polyphosphoric acid and phosphorus oxytrihalides such as phosphorus oxytrichloride.

The phosphating agent is reacted with a monohydric alcohol and with an alkylene polyol. The monohydric alcohol may generally have a hydrocarbyl group of 1 to 30 carbon atoms, or typically a hydrocarbyl group having 4 to 20 carbon atoms, such as 6 to 18 or 6 to 12 or 6 to 10 or 12 to 18 or 14 to 18 carbon atoms. The monohydric alcohol may be linear or branched; it may likewise be saturated or unsaturated.

As used in this specification, the term "hydrocarbyl substituent" or "hydrocarbyl group" is used in its ordinary sense, which is well-known to those skilled in the art. Specifically, it refers to a group having a carbon atom directly attached to the remainder of the molecule (in the case of an alcohol, directly attached to the —OH group of the alcohol) and having predominantly hydrocarbon character. Examples of hydrocarbyl groups include:

hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form a ring);

substituted hydrocarbon substituents, that is, substituents containing non-hydrocarbon groups which, in the context of this invention, do not alter the predominantly hydrocarbon nature of the substituent (e.g., halo (especially chloro and fluoro), hydroxy, alkoxy, mercapto, alkylmercapto, nitro, nitroso, and sulfoxy);

hetero substituents, that is, substituents which, while having a predominantly hydrocarbon character, in the context of this invention, contain other than carbon in a ring or chain otherwise composed of carbon atoms and encompass substituents as pyridyl, furyl, thienyl and imidazolyl. Heteroatoms include sulfur, oxygen, and nitrogen. In general, no more than two, or no more than one, non-hydrocarbon substituent will be present for every ten carbon atoms in the hydrocarbyl group; alternatively, there may be no non-hydrocarbon substituents in the hydrocarbyl group.

Suitable monohydric alcohols include various isomers of octyl alcohols, such as, notably, 2-ethylhexanol. Other examples of suitable alcohols include butanol, pentanol, hexanol, heptanol, octanol, nonanol, decanol, dodecanol, tridecanol, tetradecanol, pentadecanol, hexadecanol, heptadecanol, octadecanol, octadecenol (oleyl alcohol), nonadecanol, eicosyl-alcohol, and mixtures thereof. Examples of suitable alcohols include, for example, 4-methyl-2-pentanol, 2-ethylhexanol, isooctanol, and mixtures thereof.

Examples of commercially available alcohols include Oxo Alcohol® 7911, Oxo Alcohol® 7900 and Oxo Alcohol® 1100 of Monsanto; Alphanol® 79 of ICI; Nafol® 1620, Alfol® 610 and Alfol® 810 of Condea (now Sasol); Epal® 610 and Epal® 810 of Afton Corporation; Linevol® 79, Linevol® 911 and Dobanol® 25 L of Shell AG; Lial® 125 of Condea Augusta, Milan; Dehydad® and Lorol® of Henkel KGaA (now Cognis) as well as Linopol® 7-11 and Acropol® 91 of Ugine Kuhlmann.

The phosphating agent is also reacted with an alkylene polyol. The alkylene polyol may contain, for instance, 1 to 16, or 1 to 10, or 2 to 6, or 2 to 4 carbon atoms. In one notable embodiment, the alkylene polyol comprises 1,2-propylene glycol. Polyols generally are alcohols containing two or more alcoholic hydroxy groups, such as diols, triols, and tetrols, especially diols. Alkylene diols include those in which the two alcoholic OH groups are on adjacent carbon atoms, for example, 1,2-alkylene diols. Examples include ethylene glycol, 1,2-propylene glycol, 1,2-butylene glycol; also 1,3-propylene diol, 1,3-butylene diol, 1,4-butylene diol, 1,2-hexylene diol, 1,2-dodecylene diol, and 1,2-octadecylene diol. Triols and tetrols may be used, if desired, in combination with diols and in such amounts and under such reaction condition as may be readily determined, to restrict the amount of crosslinking that may occur. Triols include glycerol. Tetrols include pentaerythritol.

The relative amounts of the monohydric alcohol and the alkylene polyol are selected such that the mole ratio of monohydric alcohol:alkylene polyol is 0.2:0.8 to 0.8:0.2, or, in other embodiments, 0.4:0.6 to 0.7:0.3 or 0.45:0.55 to 0.67:0.33 or 0.4:0.6 to 0.6:0.4, or 0.45:0.55 to 0.55:0.45, or 0.48:0.55 to 0.52:0.48, or about 0.5:0.5, i.e., 1:1. If expressed on an equivalent basis, a 1:1 mole ratio of monool:diol would correspond to a 1:2 ratio of —OH groups. Thus, when approximately equal molar amounts of monohydric alcohol and alkylene polyol are used, there will be more hydroxy groups contributed by the polyol than by the monohydric alcohol.

The monohydric alcohol and alkylene polyol are reacted with the phosphating agent (which is alternatively known as a phosphorylating agent) in such overall amounts that the product mixture formed thereby contains phosphorus acid functionality. That is, the phosphating agent is not completely converted to its ester form but will retain at least a portion of P—OH acidic functionality, which may, if desired, be accomplished by using a sufficient amount of the phosphating agent compared with the equivalent amounts of the alcohol and polyol. In particular, in certain embodiments the phosphating agent (which may comprise phosphorus pentoxide) may be reacted with the monohydric alcohol and the alkylene polyol in a ratio of 1 to 3 or 1 to 2.5 (or 1.25 to 2 or 1.5 to 2.5 or 2.5 to 3.5) moles of hydroxyl groups per 1 mole of phosphorus from the phosphating agent. In other embodiments, the phosphating agent may be reacted with the monohydric alcohol and the alkylene polyol in a ratio of 1 to 1.75 moles of the total of monohydric alcohol plus alkylene polyol per phosphorus atom of the phosphating agent. If the phosphating agent is taken to be phosphorus pentoxide, $P_2O_5$, such that there are two P atoms per mole of phosphating agent, this ratio may be expressed as 2 to 3.5 moles of (alcohol+polyol) per mole of $P_2O_5$. In other embodiments, 2.5 to 3 moles or 3 to 3.5 moles of the total alcohol and polyol may be used per mole of phosphorus pentoxide. (This assumes that phosphorus pentoxide has the formula $P_2O_5$, rather than the alternative formula $P_4O_{10}$; appropriate ratios may be readily calculated corresponding to either formula.) The number of alcoholic OH groups per P atom may also depend on the relative amounts of the monool and diol (or higher alcohols) employed. If there is a 1:1 mole ratio of monool and diol, for instance, there will be 1.5 OH groups per mole of total alcohols, and the above-stated range of 1 to 1.75 moles of alcohols per P atom would correspond to 1.5 to 2.625 OH groups per P atom.

In one somewhat oversimplified schematic representation, the reaction of the phosphating agent with alcohol(s) may be represented as follows:

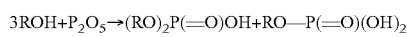

$$3ROH + P_2O_5 \rightarrow (RO)_2P(=O)OH + RO-P(=O)(OH)_2$$

where ROH represent a monohydric alcohol or part of an alkylene polyol, or two R groups may together represent the alkylene portion of an alkylene polyol. As will be seen below, the residual phosphoric acidic functionality may be reacted at least in part with an amine.

The phosphating agent may be mixed with and reacted with the monohydric alcohol and the alkylene polyol in any order. In certain embodiments, the total charge of the phosphating agent is reacted with the total charge of the monohydric alcohol plus the alkylene polyol in a single mixture.

The phosphating agent itself may also be introduced into the reaction mixture in a single portion, or it may be introduced in multiple portions. Thus, in one embodiment, a reaction product (or intermediate) is prepared wherein a portion of the phosphating agent is reacted with the monohydric alcohol and the alkylene polyol and thereafter a second charge of the phosphating agent is added.

The reaction product from the phosphating agent and the monohydric alcohol and the alkylene polyol will be a mixture of individual species, and the particular detailed compositions may depend, to some extent, on the order of addition of the reactants. The reaction mixture, however, will typically contain at least some molecules represented by the formulas (I) or (II)

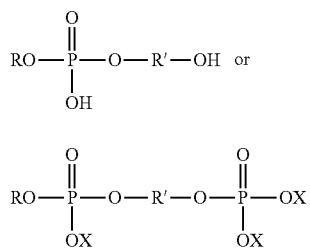

where R is an alkyl group or a hydrocarbyl group provided by the monohydric alcohol, R' is an alkylene group provided by the alkylene diol, and each X is independently R, or H, or an —R'OH group, provided that at least one X is H. In the instance where the alkylene diol is 1,2-propylene glycol, the corresponding structures may be represented by

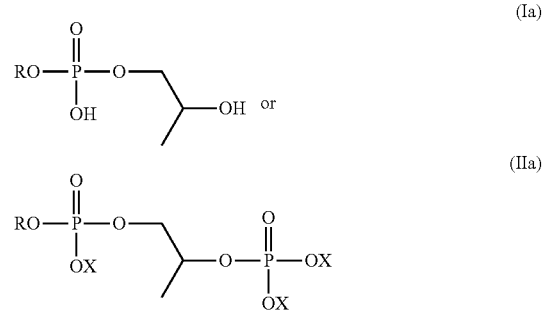

(Either orientation of the propylene glycol moiety is permitted; the methyl group may alternatively be on the other carbon atom.) Likewise, if the alkylene diol is 1,2-butylene glycol, the corresponding structures may be represented by

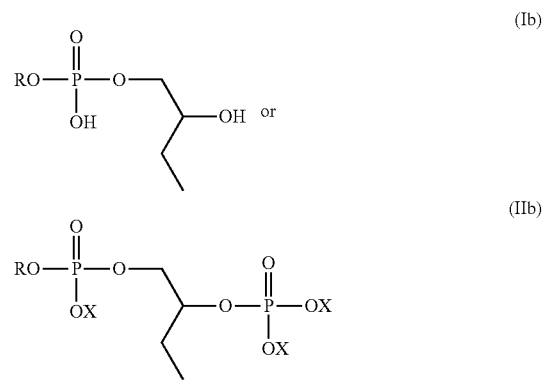

where, as before, the ethyl group may alternatively be on the other carbon atom. If diols containing 5 or more carbon atoms are used, the products will, of course, have correspondingly longer pendant hydrocarbyl groups reflecting the structures of the diols. These may be generically written (assuming the 1,2 diol structure) as

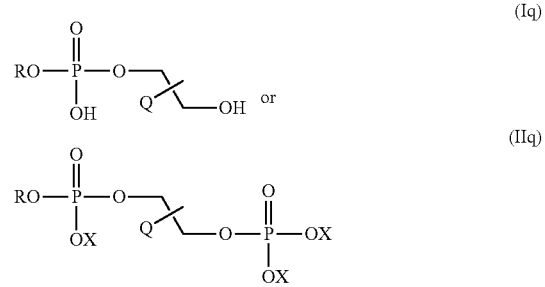

where each Q is independently a hydrocarbyl or alkyl group of, e.g., 1 to 6 or 1 to 4 or 1 to 2 carbon atoms, such as methyl or ethyl, and which may be attached to either of the carbon atoms indicated. Alternatively, Q may be hydrogen. Thus, there will be at least some, or most, or substantially all, or all molecules in which there is a residual P—OH group and in which there is both an R group from the monohydric alcohol and another group originating from the alkylene glycol. "Substantially all" means at least 90 percent by weight or at least 95, or 98, or 99 or 99.5 percent by weight, and up to 100 or 99.9 percent by weight.

There may be a variable amount of products represented by other structures, such as partially esterified materials; or fully esterified materials:

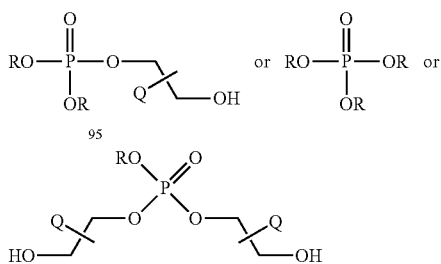

including cyclic esters such as:

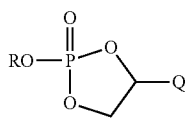

and others containing more than one unit in the ring derived from propylene glycol, as well as materials with a P—O—P linkage (pyrophosphates). There will also likely be some longer chain materials having a higher degree of condensation such as:

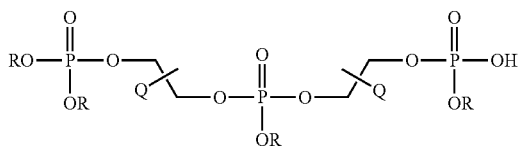

The product of the reaction as described herein, however, will likely contain little or no material containing (ether type) alkylene oxide dimers or oligomers or alkylene glycol (or diol) dimers or oligomers (initiated by a phosphorus acid). Such dimeric or oligomeric materials are likely to be formed when an alkylene oxide is employed in place of the alkylene diol of the present technology. The technology of the present invention provides materials that are characterized by a lesser amount of "alkylene oxide" (or "ether type") dimers or oligomers and thus are particularly useful in providing antiwear performance when converted to the amine salts as set forth below. In certain embodiments the reaction product is substantially free from species containing a dimeric or oligomeric moiety deriving from the dimerization or oligomerization of an alkylene oxide. By "substantially free" is meant that species containing such dimeric or oligomeric moieties may account for less than 5 percent by weight, or less than 1 percent by weight, or less than 0.1 percent by weight, or 0.01 to 0.05 percent by weight of all the phosphorus-containing species.

The reaction of the phosphating agent with the monohydric alcohol and the alkylene polyol may be effected by reacting a mixture of the reactants at 40 to 110° C., or 50 to 100° C., or 60 to 90° C., for 1 to 10, or 2 to 8, or 3 to 5 hours. The process may be carried out at reduced pressure, atmospheric pressure or above atmospheric pressure. Any water of reaction may be removed by distillation or purging with inert gas.

The product or intermediate prepared from the reaction of the phosphating agent and a monohydric alcohol and an alkylene polyol is further reacted with an amine, to form a mixture of materials that may be characterized as comprising an amine salt or salts; it may also contain materials characterized by the presence of a P—N bond. The product includes amine salts of a primary amine, a secondary amine, a tertiary amine, or mixtures thereof. In one embodiment the primary amine includes a tertiary-aliphatic primary amine. In one embodiment the amine is not an aromatic amine and, in another embodiment, it does not contain the amine nitrogen within a heterocyclic ring. In one embodiment the amine is an alkylamine, such as a dialkylamine or a monoalkylamine. A suitable dialkylamine (that is, a secondary amine) may be bis-2-ethylhexylamine. A suitable monoalkylamine (that is, a primary amine) may be 2-ethylhexylamine. In certain embodiments, the amine comprises at least one alkyl primary amine or at least one alkyl secondary amine. In one embodiment the amine comprises at least one alkyl primary amine having 6 to 18 carbon atoms. A proper selection of amine, as set forth above, can assure a product of comparatively low toxicity.

Examples of suitable primary amines include ethylamine, propylamine, butylamine, 2-ethylhexylamine, octylamine, and dodecylamine, as well as such fatty amines as n-octylamine, n-decylamine, n-dodecylamine, n-tetradecylamine, n-hexadecylamine, n-octadecylamine and oleylamine. Other useful fatty amines include commercially available fatty amines such as "Armeen®" amines (products available from Akzo Chemicals, Chicago, Ill.), such as Armeen C, Armeen O, Armeen OL, Armeen T, Armeen HT, Armeen S and Armeen SD, wherein the letter designation relates to the fatty group, such as coco, oleyl, tallow, or stearyl groups.

Examples of suitable secondary amines include dimethylamine, diethylamine, dipropylamine, dibutylamine, diamylamine, dihexylamine, diheptylamine, bis-2-ethylhexylamine, methylethylamine, ethylbutylamine, N-methyl-1-amino-cyclohexane, Armeen® 2C and ethylamylamine. The secondary amines may be cyclic amines such as piperidine, piperazine and morpholine. Examples of tertiary amines include tri-n-butylamine, tri-n-octylamine, tri-decylamine, tri-laurylamine, tri-hexadecylamine, and dimethyloleylamine (Armeen® DMOD).

In one embodiment the amines are in the form of a mixture. Examples of suitable mixtures of amines include (i) an amine with 11 to 14 carbon atoms on tertiary alkyl primary groups (that is, a primary amine with 11 to 14 carbon atoms in a tertiary alkyl group), (ii) an amine with 14 to 18 carbon atoms on tertiary alkyl primary groups (that is, a primary amine with 14 to 18 carbon atoms in a tertiary alkyl group), or (iii) an amine with 18 to 22 carbon atoms on tertiary alkyl primary groups (that is, a primary amine with 18 to 22 carbon atoms in a tertiary alkyl group). Other examples of tertiary alkyl primary amines include tert-butylamine, tert-hexylamine, tert-octylamine (such as 1,1-dimethylhexylamine), tert-decylamine (such as 1,1-dimethyloctylamine), tert-dodecylamine, tert-tetradecylamine, tert-hexadecylamine, tert-octadecylamine, tert-tetracosanylamine, and tert-octacosanylamine. In one embodiment a useful mixture of amines is "Primene® 81R" or "Primene® JMT." Primene® 81R and Primene® JMT (both produced and sold by Rohm & Haas) are mixtures of C11 to C14 tertiary alkyl primary amines and C18 to C22 tertiary alkyl primary amines respectively.

In certain embodiments the amine will comprise at least one secondary amine having 10 to 22 carbon atoms, or 12 to 20, or 14 to 18, or 16 carbon atoms, total. In certain embodiments the secondary amine will contain two alkyl groups, each having 5 to 11 carbon atoms, or 6 to 10, or 7 to 9 carbon atoms. An example is bis-2-ethylhexylamine.

In certain embodiments, the amount of amine employed in preparing the mixture of the disclosed technology will be the amount required to neutralize, in theory, all or substantially all of the acidity of the above-described phosphorus product, e.g., 90-100% or 92-98% or about 95% of the acidity. In one embodiment, as an example, the amount of acidity of the phosphorus product may be determined by titration using bromophenol blue indicator, and the amount of amine employed may be 95 percent, on an equivalent basis, of the amount of acidity determined to be present. The amount of acidity may be expressed as Total Acid Number, TAN (AS™ D 663 or 664 or 974), if desired.

In certain embodiments the amine salt will comprise a mixture of materials which will include some molecules represented by a somewhat idealized structure of formula (III)

Formula (III)

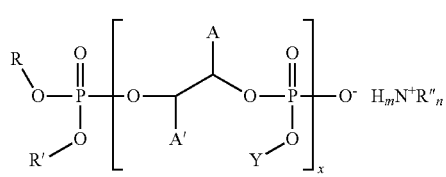

wherein A and A' are independently H, or a hydrocarbyl group containing 1 to 30 carbon atoms; each R and R″ group are independently a hydrocarbyl group; each R' is independently R, H, or a hydroxyalkyl group; Y is independently R' or a group represented by RO(R'O)P(O)O—CH(A')CH(A)- (such as RO(R'O)P(O)O—CH$_2$CH(CH$_3$)—); x is 0 to 3, provided that when x=0, R' is a hydroxyalkyl group; and m and n are both positive non-zero integers, provided that the sum of (m+n) is equal to 4.

It is evident that the anionic portion of formula (III), on the left, is a representation of an anion derived from a material of formula (I), (Ia), (II), or (IIa), and each of the foregoing representations and descriptions in connection with those formulas will also be applicable to the anionic portion of formula (III). Likewise, the cationic portion of formula (III), on the right, is a representative of a cation derived from an amine as described above.

The amine salt which includes, as an exemplar, the material of formula (III), may also contain a portion of one or more metal ions. That is, it may be a mixed amine and metal salt. In certain embodiments at least half of the valence of the anionic portion will be satisfied by an amine cation, or at least 75% or at least 90%. In one embodiment the salt does not contain a metal ion.

The metal ion, if present, may be from a mono- or divalent metal, or mixtures thereof. In one embodiment the metal ion is divalent. In one embodiment the metal of the metal ion includes lithium, sodium, potassium, calcium, magnesium, barium, copper, nickel, tin, or zinc. In one embodiment the metal of the metal ion includes lithium, sodium, calcium, magnesium, or zinc. In one embodiment the metal of the metal ion is zinc.

It is known that some of the materials described above may interact in the final formulation, so that the components of the final formulation may be different from those that are initially added. For instance, metal ions (of, e.g., a detergent) can migrate to other acidic or anionic sites of other molecules, such as the product described above. The products formed thereby, including the products formed upon employing the composition of the present invention in its intended use, may not be susceptible of easy description. Nevertheless, all such modifications and reaction products are included within the scope of the present technology; the present technology encompasses the composition prepared by admixing the components described herein.

The amine salt compositions described above will typically be used in a lubricant composition. Its amount will typically be the amount suitable to provide antiwear performance to the lubricant. Such amounts may typically be 0.3 to 3 percent by weight, or 0.5 to 1 percent, or greater than 1 to 1.9 percent, or 1.1 to 1.8 percent, or 1.2 to 1.8 percent, or 1.3 to 1.7 percent or even, in certain embodiments, 1.44 to 1.62 percent by weight.

One of the components of a lubricant composition is an oil of lubricating viscosity. These include natural and synthetic oils of lubricating viscosity, oils derived from hydrocracking, hydrogenation, or hydrofinishing, and unrefined, refined, and re-refined oils and mixtures thereof.

Natural oils include animal oils, vegetable oils, mineral oils and mixtures thereof. Synthetic oils include hydrocarbon oils, silicon-based oils, and liquid esters of phosphorus-containing acids. Synthetic oils may be produced by Fischer-Tropsch gas-to-liquid synthetic procedure as well as other gas-to-liquid oils. In one embodiment the composition of the present invention is useful when employed in a gas-to-liquid oil. Often Fischer-Tropsch hydrocarbons or waxes may be hydroisomerized. In one embodiment the base oil comprises a polyalphaolefin including a PAO-2, PAO-4, PAO-5, PAO-6, PAO-7, or PAO-8. The polyalphaolefin in one embodiment is prepared from dodecene and in another embodiment from decene. In one embodiment the oil of lubricating viscosity comprises an ester such as an adipate.

Oils of lubricating viscosity may also be defined as specified in the American Petroleum Institute (API) Base Oil Interchangeability Guidelines. In one embodiment the oil of lubricating viscosity comprises an API Group I, II, III, IV, V, VI base oil, or mixtures thereof, and in another embodiment API Group II, III, IV base oil or mixtures thereof. In another embodiment the oil of lubricating viscosity is a Group III or IV base oil and in another embodiment a Group IV base oil.

The amount of the oil of lubricating viscosity present is typically the balance remaining after subtracting from about 100 wt % the sum of the amount of the compounds of the present technology and other listed components such as friction modifier, conventional phosphorus antiwear and/or extreme pressure agent, organo-sulfide, and other performance additives. In one embodiment the lubricating composition is in the form of a concentrate and/or a fully formulated lubricant. If the phosphorus containing additive and any other performance additives are in the form of a concentrate (which may be combined with additional oil to form, in whole or in part, a finished lubricant), the ratio of the sum of the components of the lubricating composition to the oil of lubricating viscosity and/or to diluent oil include the ranges of 1:99 to about 99:1 by weight, or 80:20 to 10:90 by weight.

The lubricant formulation may contain a viscosity modifier (which is sometimes counted as a part of the oil of lubricating viscosity component). Viscosity modifiers (VM) and dispersant viscosity modifiers (DVM) are well known. Examples of VMs and DVMs may include polymethacrylates, polyacrylates, polyolefins, styrene-maleic ester copolymers, and similar polymeric substances including homopolymers, copolymers, and graft copolymers. The DVM may comprise a nitrogen-containing methacrylate polymer, for example, a nitrogen-containing methacrylate polymer derived from methyl methacrylate and dimethylaminopropyl amine.

Examples of commercially available VMs, DVMs and their chemical types may include the following: polyisobutylenes (such as Indopol™ from BP Amoco or Parapol™ from ExxonMobil); olefin copolymers (such as Lubrizol™ 7060, 7065, and 7067 from Lubrizol and Lucant™ HC-2000L and HC-600 from Mitsui); hydrogenated styrene-diene copolymers (such as Shellvis™ 40 and 50, from Shell and LZ® 7308, and 7318 from Lubrizol); styrene/maleate copolymers, which are dispersant copolymers (such as LZ® 3702 and 3715 from Lubrizol); polymethacrylates, some of which have dispersant properties (such as those in the Viscoplex™ series from RohMax, the Hitec™ viscosity modifiers from Afton, and LZ® 7702, LZ® 7727, LZ® 7725, LZ® 7720C, and LZ® 7723 from Lubrizol); olefin-graft-polymethacrylate polymers (such as Viscoplex™ 2-500 and 2-600 from RohMax); and hydrogenated polyisoprene star polymers (such as Shellvis™ 200 and 260, from Shell). Viscosity modifiers that may be used are described in U.S. Pat. Nos. 5,157,088, 5,256, 752 and 5,395,539. Other viscosity modifiers include a olefin-maleic anhydride ester copolymers, as disclosed in PCT publication WO2010/014655. The VMs and/or DVMs may be used in the functional fluid at a concentration of up to 20% by weight or even up to 60% or 70% by weight. Concentrations of 1 to 12%, or 3 to 10%, by weight may also be used.

The lubricant formulation may contain, in addition the phosphorus salt composition described above, one or more conventional phosphorus antiwear agents and/or extreme pressure agents. Alternatively, the lubricant formulation may be free from such conventional agents. The conventional phosphorus antiwear and/or extreme pressure agent may be present in an amount of 0 wt % to 10 wt %, 0 wt % to 8 wt %, 0 wt % to 6 wt %, 0.05 wt % to 2.5 wt %, 1 wt % to 2 wt %, and 0.05 wt % to 4 wt % of the lubricating composition. Suitable agents include those described in U.S. Pat. No. 3,197,405; see for instance examples 1 to 25 thereof.

The conventional phosphorus antiwear and/or extreme pressure agent may include a non-ionic phosphorus compound, an amine salt of a phosphorus compound other than those disclosed above (such as an amine salt of a mixture of monoalkyl and dialkyl phosphoric acid esters), an ammonium salt of a phosphorus compound other than those disclosed above, a metal dialkyldithiophosphate, a metal dialkylphosphate, or mixtures thereof. In one embodiment the conventional phosphorus antiwear or extreme pressure agent is selected from the group consisting of non-ionic phosphorus compound, a metal dialkyldithiophosphate, a metal dialkylphosphate, and mixtures thereof.

In one embodiment the conventional phosphorus antiwear and/or extreme pressure agent includes a metal dialkyldithiophosphate. The alkyl groups of the dialkyldithiophosphate may be linear or branched and may contain 2 to 20 carbon atoms, provided that the total number of carbons is sufficient to make the metal dialkyldithiophosphate oil soluble. The metal of the metal dialkyldithiophosphate typically includes monovalent or divalent metals. Examples of suitable metals include sodium, potassium, copper, calcium, magnesium, barium, or zinc. In one embodiment the phosphorus-containing acid, salt or ester is a zinc dialkyldithiophosphate. Examples of suitable zinc dialkylphosphates (often referred to as ZDDP, ZDP or ZDTP) include zinc di-(2-methylpropyl) dithiophosphate, zinc di-(amyl)dithiophosphate, zinc di-(1, 3-dimethylbutyl)dithiophosphate, zinc di-(heptyl)dithiophosphate, zinc di-(octyl)dithiophosphate, zinc di-(2-ethylhexyl)dithiophosphate, zinc di-(nonyl)dithiophosphate, zinc di-(decyl)dithiophosphate, zinc di-(dodecyl)dithiophosphate, zinc di-(dodecylphenyl)dithiophosphate, zinc di-(heptylphenyl)dithiophosphate, and ZDDPs prepared from mixed alcohols such as methylpropyl and amyl alcohols, 2-ethylhexyl and isopropyl alcohols, or 4-methyl-2-pentyl and isopropyl alcohols; or mixtures thereof.

In one embodiment the conventional phosphorus antiwear and/or extreme pressure agent includes a metal hydrocarbylphosphate or dihydrocarbylphosphate. The hydrocarbyl group of the metal dialkylphosphate includes a straight-chain or a branched alkyl group, a cyclic alkyl group, a straight-chain or a branched alkenyl group, an aryl group, or an arylalkyl group. In one embodiment the hydrocarbyl group of the metal dialkylphosphate is an oil soluble alkyl group. The alkyl group typically includes about 1 to about 40, or about 4 to about 40, or about 4 to about 20, or about 6 to about 16 carbon atoms. Examples of suitable hydrocarbyl or alkyl groups are listed in WO 2008/094759, paragraphs 0069 through 0076.

In one embodiment the metal hydrocarbylphosphate or dihydrocarbylphosphate includes a metal salt of a mono-alkyl phosphate, and in another embodiment a metal salt of a dialkyl phosphate. In one embodiment the metal of the metal hydrocarbylphosphate or dihydrocarbylphosphate is a monovalent metal, in another embodiment the metal is divalent, and in another embodiment the metal is trivalent. The metal of the metal hydrocarbylphosphate or dihydrocarbylphosphate may include aluminum, calcium, magnesium, strontium, chromium, iron, cobalt, nickel, zinc, tin, manganese, silver, or mixtures thereof. In one embodiment the metal is zinc.

In one embodiment the lubricating composition further comprises an organo-sulfide. In one embodiment the organo-sulfide comprises at least one of a polysulfide, thiadiazole compound, or mixtures thereof. In different embodiments, the organo-sulfide is present in a range of 0 wt % to 10 wt %, 0.01 wt % to 10 wt %, 0.1 wt % to 8 wt %, 0.25 wt % to 6 wt %, 2 wt % to 5 wt %, or 3 wt % to 5 wt % of the lubricating composition.

Examples of a thiadiazole include 2,5-dimercapto-1,3,4-thiadiazole, or oligomers thereof, a hydrocarbyl-substituted 2,5-dimercapto-1,3,4-thiadiazole, a hydrocarbylthio-substituted 2,5-dimercapto-1,3,4-thiadiazole, or oligomers thereof. The oligomers of hydrocarbyl-substituted 2,5-dimercapto-1, 3,4-thiadiazole typically form by forming a sulfur-sulfur bond between 2,5-dimercapto-1,3,4-thiadiazole units to form oligomers of two or more of said thiadiazole units. Further examples of thiadiazole compounds are found in WO 2008/094759, paragraphs 0088 through 0090.

The organosulfide may alternatively be a polysulfide. In one embodiment at least about 50 wt % of the polysulfide molecules are a mixture of tri- or tetra-sulfides. In other embodiments at least about 55 wt %, or at least about 60 wt % of the polysulfide molecules are a mixture of tri- or tetra-sulfides. The polysulfides include sulfurized organic polysulfides from oils, fatty acids or ester, olefins or polyolefins.

Oils which may be sulfurized include natural or synthetic oils such as mineral oils, lard oil, carboxylate esters derived from aliphatic alcohols and fatty acids or aliphatic carboxylic acids (e.g., myristyl oleate and oleyl oleate), and synthetic unsaturated esters or glycerides.

Fatty acids include those that contain 8 to 30, or 12 to 24 carbon atoms. Examples of fatty acids include oleic, linoleic, linolenic, and tall oil. Sulfurized fatty acid esters prepared from mixed unsaturated fatty acid esters such as are obtained from animal fats and vegetable oils, including tall oil, linseed oil, soybean oil, rapeseed oil, and fish oil.

The polysulfide may also be derived from an olefin derived from a wide range of alkenes, typically having one or more double bonds. The olefins in one embodiment contain 3 to 30 carbon atoms. In other embodiments, olefins contain 3 to 16, or 3 to 9 carbon atoms. In one embodiment the sulfurized olefin includes an olefin derived from propylene, isobutylene, pentene, or mixtures thereof. In one embodiment the polysulfide comprises a polyolefin derived from polymerizing, by known techniques, an olefin as described above. In one embodiment the polysulfide includes dibutyl tetrasulfide, sulfurized methyl ester of oleic acid, sulfurized alkylphenol, sulfurized dipentene, sulfurized dicyclopentadiene, sulfurized terpene, and sulfurized Diels-Alder adducts; phosphosulfurized hydrocarbons.

In one embodiment the lubricating composition further comprises a friction modifier. In different embodiments, the friction modifier is present in an amount of 0 wt % to 7 wt %, 0.1 wt % to 6 wt %, 0.25 wt % to 5 wt %, or 0.5 wt % to 5 wt % of the lubricating composition.

The friction modifier includes fatty amines, borated glycerol esters, fatty acid amides, non-borated fatty epoxides, borated fatty epoxides, alkoxylated fatty amines, borated alkoxylated fatty amines, metal salts of fatty acids, fatty imidazolines, metal salts of alkyl salicylates (which may also be referred to as a detergent), metal salts of sulfonates (which may also be referred to as a detergent), condensation products of carboxylic acids or polyalkylene-polyamines, or amides of hydroxyalkyl compounds. In one embodiment the friction modifier includes a fatty acid ester of glycerol. The fatty acids may contain 6 to 24, or 8 to 18 carbon atoms. In one embodiment the friction modifier may comprise the product of isostearic acid with tetraethylenepentamine. A more detailed list of possible friction modifiers is found in WO 2008/094759, paragraphs 0100 through 0113.

The composition of the invention optionally further includes at least one other performance additive. The other performance additives include metal deactivators, detergents, dispersants, borated dispersants, antioxidants, corrosion inhibitors, foam inhibitors, demulsifiers, pour point depressants, seal swelling agents, and mixtures thereof. Foam inhibitors may be useful in that, in some embodiments, the phosphorus compounds of the present technology may tend to lead to enhanced foam formation, particularly when the phosphorus compounds are present in higher concentrations, such as 0.5 percent or greater, or 1.0 percent or greater, e.g. 1.1 to 3 percent by weight. In different embodiments, the total combined amount of the other performance additive compounds is present at 0 wt % to 25 wt %, about 0.1 wt % to 15 wt %, or 0.5 wt % to 10 wt %, of the lubricating composition. Although one or more of the other performance additives may be present, it is common for the other performance additives to be present in different amounts relative to each other.

Antioxidants include molybdenum compounds such as molybdenum dithiocarbamates, sulfurized olefins, hindered phenols, aminic compounds such as alkylated diphenylamines (typically di-nonyl diphenylamine, octyl diphenylamine, or di-octyl diphenylamine).

Detergents include neutral or overbased detergents, Newtonian or non-Newtonian, basic salts of alkali, alkaline earth or transition metals with one or more of a phenate, a sulfurized phenate, a sulfonate, a carboxylic acid, a phosphorus acid, a mono- and/or a di-thiophosphoric acid, a saligenin, an alkylsalicylate, and a salixarate.

Dispersants include N-substituted long chain alkenyl succinimides, as well as Mannich condensation products as well as post-treated versions thereof. Post-treated dispersants include those by reaction with urea, thiourea, dimercaptothiadiazoles, carbon disulfide, aldehydes, ketones, carboxylic acids, hydrocarbon-substituted succinic anhydrides, nitriles, epoxides, boron compounds, and phosphorus compounds. In one embodiment the dispersant includes a borated polyisobutylene succinimide. Typically the number average molecular weight of the polyisobutylene ranges from about 450 to 5000, or 550 to 2500. In different embodiments, the dispersant is present in an amount of 0 wt % to 10 wt %, 0.01 wt % to 10 wt %, or 0.1 wt % to 5 wt % of the lubricating composition.

Corrosion inhibitors include octylamine octanoate, condensation products of dodecenyl succinic acid or anhydride, condensation products of a fatty acid such as oleic acid with a polyamine, or a thiadiazole compound described above. Metal deactivators include derivatives of benzotriazoles (typically tolyltriazole), 1,2,4-triazoles, benzimidazoles, 2-alkyldithiobenzimidazoles or 2-alkyldithiobenzothiazoles.

Foam inhibitors include copolymers of ethyl acrylate and 2-ethylhexylacrylate and optionally vinyl acetate. Demulsifiers include trialkyl phosphates, polyethylene glycols, polyethylene oxides, polypropylene oxides and (ethylene oxide-propylene oxide) polymers. Pour point depressants include esters of maleic anhydride-styrene, polymethacrylates, polyacrylates, or polyacrylamides. Seal swell agents include Exxon Necton-37™ (FN 1380) and Exxon Mineral Seal Oil (FN 3200).

In one embodiment the lubricating composition described herein may be a grease, and such compositions typically will further comprise a grease thickener. The grease thickener includes materials derived from (i) inorganic powders such as clay, organo-clays, bentonite, fumed silica, calcite, carbon black, pigments, copper phthalocyanine or mixtures thereof, (ii) a carboxylic acid and/or ester (such as a mono- or poly-carboxylic acid and/or ester thereof), (iii) a polyurea or diurea, or (iv) mixtures thereof. A detailed description of specific grease thickeners is found in WO 2008/094759, paragraphs 0135 through 0145. A grease composition may also contain one or more metal deactivators, antioxidants, anti-wear agents, rust inhibitors, viscosity modifiers, extreme pressure agents (as described above) or a mixture of two or more thereof.

In one embodiment the present technology provides a method of lubricating a driveline device (such as a gear, axle, or transmission) comprising supplying to the driveline device a lubricating composition disclosed herein. The driveline device may comprise at least one of a gear, a gearbox, an axle gear, a traction drive transmission, an automatic transmission or a manual transmission. In one embodiment the driveline device is a manual transmission or a gear, a gearbox, or an axle gear. The automatic transmission may be a continuously variable transmission (CVT), an infinitely variable transmission (IVT), a toroidal transmission, a continuously slipping torque converted clutch (CSTCC), a stepped automatic transmission, or a dual clutch transmission (DCT).

In one embodiment the invention provides for the use of the lubricating composition disclosed herein in gears and transmissions to impart at least one of antiwear performance, extreme pressure performance, acceptable deposit control, acceptable oxidation stability, and reduced odor.

The amount of each chemical component described is presented exclusive of any solvent or diluent oil, which may be customarily present in the commercial material, that is, on an active chemical basis, unless otherwise indicated. However, unless otherwise indicated, each chemical or composition referred to herein should be interpreted as being a commercial grade material which may contain the isomers, by-products, derivatives, and other such materials which are normally understood to be present in the commercial grade.

EXAMPLES

Preparative Example 1

2-Ethylhexanol (100 g) and 1,2-propanediol (58.5 g) are mixed in a reaction flask and heated under a gentle stream of nitrogen to 60° C. with stirring. Phosphorus pentoxide (74 g) is added in several increments with stirring. Upon completion of the addition of the phosphorus pentoxide, the reaction mixture is heated to 90° C. and maintained at this temperature for 3 hours, and then cooled to 48° C. Approximately one half of the reaction mixture is taken for further reaction; to this amount, bis-2-ethylhexylamine (110 g) is added dropwise over a period of 1 hour. The resulting mixture is heated to 75° C. and maintained at this temperature for 3 hours. The reaction product is used without further purification.

Preparative Example 2

2-Ethylhexanol (200 g) and 1,2-propanediol (117 g) are mixed in a reaction flask and heated under a gentle stream of nitrogen to 60° C. with stirring. Phosphorus pentoxide (146 g) is added in several increments with stirring. Upon completion of the addition of the phosphorus pentoxide, the reaction mixture is heated to 90° C. and maintained at this temperature for 5.5 hours. The reaction mixture is cooled to 80° C. and phosphorus pentoxide (44 g) is again added in several increments with stirring. Upon completion of the addition of the phosphorus pentoxide, the reaction mixture is held at 80° C. for 3 hours and then cooled to 48° C. Approximately two-thirds of the reaction mixture is taken for further reaction; to this amount, bis-2-ethylhexylamine (314 g) is added dropwise over a period of 50 minutes, with stirring. The resulting mixture is heated to 75° C. and maintained at this temperature for 3 hours. The reaction product is used without further purification.

Reference Preparative Example 3 (Using Propylene Oxide)

A C8 alcohol is heated to 60° C. under a gentle stream of nitrogen with stirring. Phosphorus pentoxide is added in several increments. Upon completion of the addition of the phosphorus pentoxide, the reaction mixture is heated to 90° C. and maintained at this temperature for 6 hours. The reaction mixture is cooled to 50° C. and propylene oxide is added over a period of 1.5 hours. The reaction mixture is warmed to 70° C. and maintained at this temperature for 2 hours. The reaction mixture is then vacuum stripped at 70° C. for 1 hour. The reaction mixture is cooled to 50° C., and additional phosphorus pentoxide is added in several increments over a period of 1.5 hours. The reaction mixture is heated to 80° C., stirred for 3 hours, and filtered. The filtrate is heated to 45° C. under a gentle stream of nitrogen. Bis-2-ethylhexylamine is added dropwise over a period of 2 hours. The reaction mixture is warmed to 75° C. and held at this temperature for 2.5 hours. The reaction product is used without further purification.

Preparative Example 4

90.12 g of 1,2-butanediol and 130 g of 2-ethylhexanol are mixed in a reaction flask and heated under a gentle stream of nitrogen to 60° C. with stirring. 94.6 g of phosphorus pentoxide is added in several increments with stirring. Upon completion of the addition of phosphorus pentoxide, the reaction mixture is heated to 90° C. and maintained at this temperature for 3 hours, and then cooled to 48° C. 290 g of bis-2-ethylhexylamine is added dropwise to the reaction mixture over a period of 50 minutes, with stirring. The mixture is heated to 75° C. and maintained at this temperature for 3 hours. The reaction product is used without further purification.

Preparative Example 5

90.12 g of 1,2-butanediol and 130 g of 2-ethylhexanol are mixed in reaction flask and heated under a gentle stream of nitrogen to 60° C. with stirring. 94.6 g of phosphorus pentoxide is added in several increments with stirring. Upon completion of the addition of phosphorous pentoxide, the reaction mixture is heated to 90° C. and maintained at this temperature for 3 hours. The reaction mixture is cooled to 80° C. and 32 g of phosphorus pentoxide is added in several increments with stirring. Upon completion of the addition of the phosphorus pentoxide, the reaction mixture is held at 80° C. for 3 hours and then cooled to 48° C. 399 g of bis-2-ethylhexylamine is added dropwise to the reaction mixture over a period of 50 minutes with stirring. The mixture is heated to 75° C. and maintained at this temperature for 3 hours. The reaction product is used without further purification.

Preparative Example 6

152 g of propylene glycol (that is, 1,2-propanediol) and 130 g 2-ethylhexanol are mixed in a reaction flask and heated under a gentle stream of nitrogen to 60° C. with stirring. 141.9 g of phosphorus pentoxide is added in several increments with stirring. Upon completion of the addition of phosphorus pentoxide, the reaction mixture is heated to 90° C. and maintained at this temperature for 3 hours, and then cooled to 48° C. 402.2 g of bis-2-ethylhexylamine is added dropwise to the reaction mixture over a period of 50 minutes with stirring. The mixture is heated to 75° C. and maintained at this temperature for 3 hours. The reaction product is used without further purification.

Preparative Example 7

258 g of 1,2-hexadecanediol and 130 g of 2-ethylhexanol are mixed in a reaction flask and heated under a gentle stream of nitrogen to 60° C. with stirring. 95 g of phosphorus pentoxide is added in several increments with stirring. Upon completion of the addition of phosphorus pentoxide, the reaction mixture is heated to 90° C. and maintained at this temperature for 3 hours, and then cooled to 48° C. 278 g of bis-2-ethylhexylamine is added dropwise to the reaction mixture over a period of 50 minutes with stirring. The mixture is heated to 75° C. and maintained at this temperature for 3 hours. The reaction product is used without further purification.

Preparative Example 8

(a) 2-Ethylhexanol (1199.4 g) and 1,2-propanediol (i.e., propylene glycol, 700 g) are mixed in a flask equipped with a mechanical stirrer, nitrogen inlet, thermocouple, and reflux condenser. The alcohols are heated under a gentle stream of nitrogen to 60° C. with stirring. Phosphorus pentoxide (872.7 g) is added in eleven increments with stirring over the course of about 2.5 hours. Upon completion of the addition of the phosphorus pentoxide, the reaction mixture is heated to 90° C. and maintained at this temperature for 3 hours, and then cooled to room temperature. The product is a colorless, clear liquid.

(b) Material from step (a), 2744.1 g, is heated to 60° C. and 288.3 g phosphorus pentoxide is added in three portions over 1 hour, then the mixture is maintained at 80° C. for 3 hours.

(c) 476 g of material from step (b) is placed in a 1-L round-bottom flask equipped with a mechanical stirrer, nitrogen inlet, water-cooled condenser, and thermocouple. 2-Ethylhexylamine, 248.4 g, is added dropwise over a period of 1.5 hours, the resulting exothermic reaction being controlled by cooling the vessel with cold water. Thereafter, the reaction mixture is heated to 75° C. and maintained at this temperature for 3 hours. The resulting product is a pale yellow sticky liquid.

Preparative Example 9

(a) Preparative Example 8 is substantially repeated except that the amount of 2-ethylhexanol is 154.9 g, the amount of 1,2-propanediol is 182 g, and there is also initially present in the reaction mixture 121.6 g 4-methyl-2-pentanol. The amount of phosphorus pentoxide used is 225.6 g.

(b) Material from step (a), 644 g, is heated to 60° C. and 56.6 g phosphorus pentoxide is added in three portions over 1 hour, then the mixture is maintained at 80° C. for 3 hours.

(c) 604.7 g of material from step (b) is placed in a 1-L round-bottom flask equipped with a mechanical stirrer, nitrogen inlet, water-cooled condenser, and thermocouple. 2-Ethylhexylamine, 309.7 g, is added dropwise over a period of 1.5 hours, the resulting exothermic reaction being controlled by cooling the vessel with cold water. Thereafter, the reaction mixture is heated to 75° C. and maintained at this temperature for 3 hours. The resulting product is a pale yellow sticky liquid.

Preparative Example 10

(a) Preparative Example 8 is substantially repeated except that the amount of propylene glycol is 182 g, the amount of phosphorus anhydride is 225.3 g, and the 2-ethylhexanol is replaced by 244.5 g 2-methyl-2-pentanol.

(b) Material from step (a), 611.1 g, is heated to 60° C. and 70.2 g phosphorus pentoxide is added in three portions over 1 hour, then the mixture is maintained at 80° C. for 3 hours.

(c) 618 g of material from step (b) is placed in a 1-L round-bottom flask equipped with a mechanical stirrer, nitrogen inlet, water-cooled condenser, and thermocouple. 2-Ethylhexylamine, 379 g, is added dropwise over a period of 1.5 hours, the resulting exothermic reaction being controlled by cooling the vessel with cold water. Thereafter, the reaction mixture is heated to 75° C. and maintained at this temperature for 3 hours. The resulting product is a pale yellow sticky liquid.

Preparative Example 11

Preparative Example 8 is substantially repeated except that in step (a), amount of 2-ethylhexanol is 276 g, the amount of propylene glycol is 80.7 g, and the amount of phosphorus pentoxide is 150 g. From the resulting mixture, 482.7 g is taken and reacted (step (b)) with a second addition of 47.8 g phosphorus pentoxide. The reaction from the second addition (499 g) is reacted with 47.8 g 2-ethylhexylamine (step (c)).

Preparative Example 12

Preparative Example 8 is substantially repeated except that in step (a), amount of 2-ethylhexanol is 137.6 g, the amount of propylene glycol is 80.3 g, and the amount of phosphorus pentoxide is 150 g, and there is also present 107.8 g 2-methyl-2-pentanol. In a second addition, 47.8 g phosphorus pentoxide is added. The product is reacted with 440.1 g 2-ethylhexylamine.

Preparative Example 13

Preparative Example 8 is substantially repeated except that in step (a), the amount of propylene glycol is 80.3 g, the amount of phosphorus pentoxide is 150 g, and 216.1 g 2-methyl-2-pentanol is used in place of the 2-ethylhexanol. From the resulting mixture, 417.6 g is taken and reacted (step (b)) with a second addition of 48 g phosphorus pentoxide. The reaction from the second addition (440.1 g) is reacted with 261.5 g 2-ethylhexylamine (step (c)).

Preparative Example 14

Preparative Example 8 is substantially repeated except that in step (a), the amount of propylene glycol is 32.17 g, the amount of phosphorus pentoxide is 100 g, and the amount of 2-ethylhexanol is 220.07 g. In a second addition, 22.01 g phosphorus anhydride is added. The product is reacted with an amount of 2-ethyhexlamine calculated to neutralize 95% of the TAN of the reaction mixture.

Preparative Example 15

Preparative Example 12 is substantially repeated except that in step (a), amount of 2-ethylhexanol is 110.04 g, the amount of propylene glycol is 32.17 g, and the amount of phosphorus pentoxide is 100 g, and there is also present 86.33 g 2-methyl-2-pentanol. In a second addition, 22.01 g phosphorus pentoxide is added. The product is reacted with an amount of 2-ethylhexylamine calculated to neutralize 95% of the TAN of the reaction mixture.

Preparative Example 16

Preparative Example 8 is substantially repeated except that in step (a), the amount of propylene glycol is 32.17 g, the amount of phosphorus pentoxide is 100 g, and the 2-ethylhexanol is replaced by 172.65 g 2-methyl-2-pentanol. In a second addition, 22.01 g phosphorus pentoxide is added. The product is reacted with an amount of 2-ethyhexylamine calculated to neutralize 95% of the TAN of the reaction mixture.

Preparative Example 17

In a "one-pot" procedure, in equipment analogous to that of Preparative Example 8, 45.6 g propylene glycol and 77.8 g 2-ethylhexanol are mixed and 75 g of phosphorus pentoxide is added over 2 hours. The mixture is heated to 90° C. and maintained at temperature for 3 hours. The reaction mixture is left overnight at room temperature, then heated to 48° C. To this is added 71.9 g 2-ethylhexylamine, dropwise, and the mixture warmed to 75° C. and maintained at that temperature for 3 hours.

The materials of Preparative Example 1 and Preparative Example 2 are each provided, in the amounts indicated, to a test formulation comprising the following additional components:

Poly alpha olefin oil of lubricating viscosity (remainder to bring the total to 100%)
Functionalized methacrylic copolymer viscosity modifier, 20.4% (including 21% diluent oil)
Polyisobutylene viscosity modifier, 11.4%

Sulfurized olefin antiwear agent(s), 4%
Succinic ester corrosion inhibitor, 2.5% (including 49% oil)
Borated succinimide dispersant 1.25% (including 33% oil)
Long chain primary amine, 0.5%
Commercial antifoam agent(s), 0.1-0.15%
Additional diluent oil, about 1%

| Additive, % | Ex. 1 | Ex. 2 | Ex. 3 (reference) |
|---|---|---|---|
| Preparative Ex. 1 | 1.62 | | |
| Preparative Ex. 2 | | 1.44 | |
| Commercial[a] | | | 1.5 |
| Test Results[b]: | | | |
| D130 | 1B | 1B | 1B |
| D4172 (mm) | 0.37 | 0.43 | 0.53 |
| D665_A | Pass/Pass | Pass/Pass | Pass/Pass |
| D665_B | Pass/Pass | Pass/Pass | Pass/Pass |
| D6121 | Pass | Pass | Pass |

[a]Commercial material similar to Reference Preparative Example 3, prepared using polypropylene oxide.
[b]ASTM D130: a test to measure the corrosiveness of fuel oil, lubricating oils, and other petroleum products.
ASTM D4172: a test to evaluate the anti-wear properties of fluid lubricants in sliding contact by means of a four-ball wear test machine.
ASTM D665 A: a test to evaluate the ability of oils to aid in preventing the rusting of ferrous parts, should water become mixed with the oil
ASTM D665 B: a test to evaluate the ability of oils to aid in preventing the rusting of ferrous parts should sea water become mixed with the oil
ASTM D6121: a hypoid wear test known to the industry as L-37 (non- lubrited), to evaluate the load carrying wear in an axle under high speed/low torque and low speed/high torque conditions, using the procedure for non-lubrited gear batch V1L500/P4T813.

The results show that the materials of the present technology provide equal performance in corrosion tests and equal or better wear performance as measured by the D4172 test and the above screen test, compared to the commercial material prepared using propylene oxide. And, as shown above, the process for preparing the materials of the present technology is significantly improved in terms of reaction cycle time and synthetic complexity, compared to that of the commercial material Each of the documents referred to above is incorporated herein by reference. The mention of any document is not an admission that such document qualifies as prior art or constitutes the general knowledge of the skilled person in any jurisdiction. Except in the Examples, or where otherwise explicitly indicated, all numerical quantities in this description specifying amounts of materials, reaction conditions, molecular weights, number of carbon atoms, and the like, are to be understood as modified by the word "about." It is to be understood that the upper and lower amount, range, and ratio limits set forth herein may be independently combined. Similarly, the ranges and amounts for each element of the invention can be used together with ranges or amounts for any of the other elements. As used herein, the expression "consisting essentially of" permits the inclusion of substances that do not materially affect the basic and novel characteristics of the composition under consideration.

What is claimed is:

1. A process for preparing a salt of a hydroxy-substituted di-ester of phosphoric acid, comprising:
   (a) reacting a phosphating agent comprising phosphorus pentoxide with a monohydric alcohol having about 4 to about 20 carbon atoms and with an 1,2-alkylene diol, wherein the mole ratio of monohydric alcohol:1,2-alkylene diol is about 0.2:0.8 to about 0.8:0.2, whereby the product mixture formed thereby contains phosphorus acid functionality; and
   (b) reacting the product mixture of step (a) with an amine comprising at least one alkyl primary amine or at least one alkyl secondary amine;
   wherein the 1,2-alkylene diol comprises 1,2-propylene glycol.

2. The process of claim 1 wherein the monohydric alcohol comprises 2-ethylhexanol.

3. The process of claim 1 wherein the mole ratio of monohydric alcohol:1,2-alkylene diol is about 0.4:0.6 to about 0.7:0.3.

4. The process of claim 1 wherein the mole ratio of monohydric alcohol:1,2-alkylene diol is about 0.45:0.55 to about 0.67:0.33.

5. The process of claim 1 wherein the mole ratio of monohydric alcohol:1,2-alkylene diol is about 0.45:0.55 to about 0.55:0.45.

6. The process of claim 1 wherein the phosphating agent comprises phosphorus pentoxide and about 2 to about 3.5 moles of the total of monohydric alcohol plus 1,2-alkylene diol are reacted per 1 mole of the phosphorus pentoxide (calculated as $P_2O_5$).

7. The process of claim 6 wherein about 2.5 to about 3.5 moles of the total of monohydric alcohol plus 1,2-alkylene diol are reacted per 1 mole of an initial charge of phosphorus pentoxide, and the intermediate product formed thereby is subsequently reacted with a second charge of phosphorus pentoxide.

8. A process for preparing a salt of a hydroxy-substituted di-ester of phosphoric acid, comprising:
   (a) reacting a phosphating agent comprising phosphorus pentoxide with a monohydric alcohol having about 4 to about 20 carbon atoms and with a 1,2-alkylene diol, wherein the mole ratio of monohydric alcohol:1,2-alkylene diol is about 0.2:0.8 to about 0.8:0.2, whereby the product mixture formed thereby contains phosphorus acid functionality; and
   (b) reacting the product mixture of step (a) with an amine comprising at least one alkyl primary amine or at least one alkyl secondary amine;
   wherein at least a portion of the monohydric alcohol is reacted with the phosphating agent before the 1,2-alkylene diol is introduced to the reaction mixture.

9. The process of claim 1, wherein the product mixture prepared by step (a) comprises at least some molecules represented by the formulas

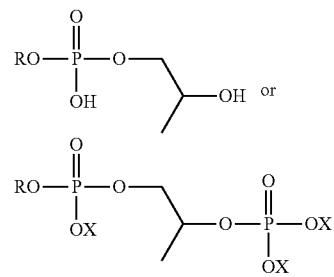

where R is an alkyl group provided by the monohydric alcohol and each X is independently R, or H, or a —$C_3H_6OH$ group, provided that at least one X is H.

10. The process of claim 1 wherein the reaction of step (a) is conducted at about 40° C. to about 110° C.

11. The process of claim 1 wherein the product mixture prepared by step (a) is substantially free from species containing a dimeric or oligomeric moiety deriving from the dimerization or oligomerization of an alkylene oxide.

12. The process of claim 1 wherein the amine comprises at least one alkyl primary amine having about 6 to about 18 carbon atoms.

13. The process of claim 1 wherein the amine comprises at least one secondary amine having about 10 to about 22 carbon atoms.

14. The process of claim 1 wherein the product mixture prepared by step (a) is reacted with a basic metal-containing compound in addition to an amine.

15. The product prepared by the process of claim 1.

16. A composition comprising an alkyl primary amine salt or an alkyl secondary amine salt of a phosphorus-containing composition which phosphorus-containing composition comprises at least some molecules represented by the formula

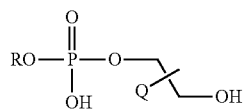

where R is an alkyl group having about 4 to about 20 carbon atoms, Q is hydrogen or an alkyl group of 1 to about 6 carbon atoms, further provided that said composition is substantially free from species containing a dimeric or oligomeric moiety derived from the dimerization or oligomerization of an alkylene oxide.

17. A lubricant comprising an oil of lubricating viscosity and the product of claim 15.

18. A method for lubricating a gear, an axle, or a transmission, comprising supplying thereto the lubricant of claim 17.

19. A lubricant comprising an oil of lubricating viscosity and the composition of claim 16.

20. A method for lubricating a gear, an axle, or a transmission, comprising supplying thereto the lubricant of claim 19.

* * * * *